US012295951B2

(12) United States Patent
Ribeiro et al.

(10) Patent No.: US 12,295,951 B2
(45) Date of Patent: May 13, 2025

(54) COMPOUNDS FOR USE IN A METHOD OF TREATING OR PREVENTING NEUROLOGICAL AND/OR PSYCHIATRIC DISORDERS

(71) Applicants: The Beckley Foundation, Oxford (GB); D'Or Institute for Research and Education—IDOR, Botafogo-RJ (BR); Universidade Federal do Rio Grande do Norte, Natal-RN (BR)

(72) Inventors: Sidarta Ribeiro, Natal-NR (BR); Amanda Feilding, Oxford (GB)

(73) Assignee: The Beckley Foundation, Oxford (GB)

( * ) Notice: Subject to any disclaimer, the term of this patent is extended or adjusted under 35 U.S.C. 154(b) by 389 days.

(21) Appl. No.: 17/631,876

(22) PCT Filed: Jul. 30, 2020

(86) PCT No.: PCT/EP2020/071525
§ 371 (c)(1),
(2) Date: Jan. 31, 2022

(87) PCT Pub. No.: WO2021/019023
PCT Pub. Date: Feb. 4, 2021

(65) Prior Publication Data
US 2022/0273644 A1 Sep. 1, 2022

(30) Foreign Application Priority Data
Aug. 1, 2019 (GB) ...................................... 1911024

(51) Int. Cl.
*A61K 31/48* (2006.01)
*A61K 45/06* (2006.01)
*A61P 25/16* (2006.01)
*A61P 25/22* (2006.01)
*A61P 25/28* (2006.01)
*A61P 25/36* (2006.01)

(52) U.S. Cl.
CPC .............. *A61K 31/48* (2013.01); *A61K 45/06* (2013.01); *A61P 25/28* (2018.01); *A61P 25/16* (2018.01); *A61P 25/22* (2018.01); *A61P 25/36* (2018.01)

(58) Field of Classification Search
CPC ..................................................... A61K 31/48
See application file for complete search history.

(56) References Cited

U.S. PATENT DOCUMENTS

| 3,883,655 A | 5/1975 | Fuxe |
| 4,524,072 A | 6/1985 | Zivin |
| 8,277,842 B1 | 10/2012 | Kaplan |

FOREIGN PATENT DOCUMENTS

| WO | WO-2002013867 A2 * | 8/2001 | ............. A61K 45/00 |
| WO | WO 2005/067930 A2 | 7/2005 | |
| WO | WO-2016145193 A1 * | 9/2016 | ............. A61K 31/13 |
| WO | WO 2019/246532 A1 | 12/2019 | |

OTHER PUBLICATIONS

Battaglia et al (CNS Drugs Oct. 2000; 14 (4): 267-287) (Year: 2000).*
Maeve A. Caldwell et al., Lisuride prevents learning and memory impairment and attenuates the increase in extracellular dopamine induced by transient global cerebral ischemia in rats, Brain Research, Jun. 17, 1997, 305-318, vol. 771, Elsevier, Netherlands.
Peter Gasser et al., LSD-assisted psychotherapy for anxiety associated with a life-threatening disease: A qualitative study of acute and sustained subjective effects, J Psychopharmacol., Nov. 11, 2014, 57-68, vol. 29, Sage Journals, United States of America.
Neiloufar Family et al., Safety, tolerability, pharmacokinetics, and pharmacodynamics of low dose lysergic acid diethylamide (LSD) in healthy older volunteers, Psychopharmacology, Dec. 18, 2019, 841-853, vol. 237, Springer, Germany.
PCT/EP2020/071525. International Preliminary Report on Patentability. Feb. 1, 2022.
PCT/EP2020/071525. International Search Report. Oct. 10, 2020/.
PCT/EP2020/071525. Search Strategy. Oct. 26, 2020.
PCT/EP2020/071525. Written Opinion of the International Searching Authority. Oct. 26, 2020.

* cited by examiner

Primary Examiner — John S Kenyon
Assistant Examiner — Rehana Ismail
(74) Attorney, Agent, or Firm — CALYX LAW; Graham Pechenik

(57) ABSTRACT

The present invention relates to compounds, i.e. ergoline derivatives, such as lysergic acid diethylamide, or pharmaceutically acceptable salts thereof for use in a method of treating (alleviating), preventing, reducing the symptoms of and/or slowing down the progression of a neurological and/or psychiatric disorder, such as mild cognitive impairment or Alzheimer's disease. In some aspects, the present invention relates to a method of treating, preventing, reducing the symptoms of and/or slowing down the progression of a neurological and/psychiatric disorder, which uses an ergoline derivative such as lysergic acid diethylamide or a pharmaceutically acceptable salt thereof.

20 Claims, 7 Drawing Sheets

A

Figure 1:
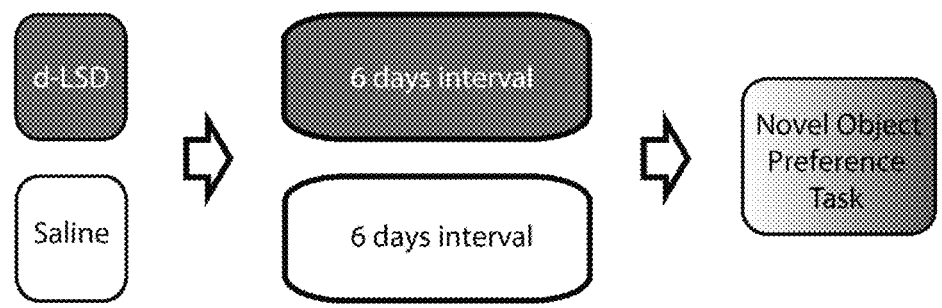
Figure 1:
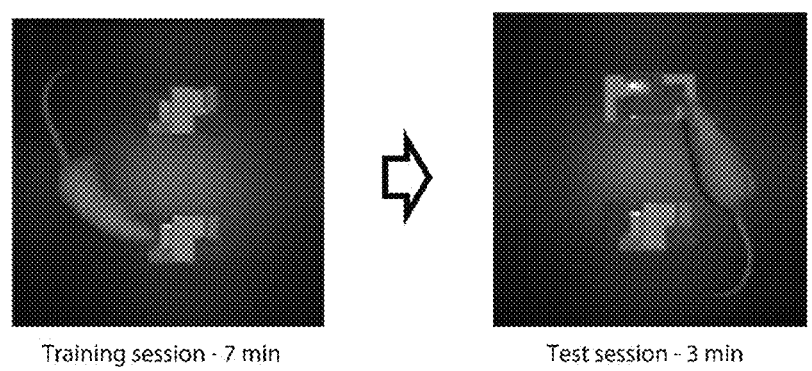

Experimental design of d-LSD treatment of young, adult and old rats

B

Novel object preference task

Training session - 7 min    Test session - 3 min

COMPOUNDS FOR USE IN A METHOD OF TREATING OR PREVENTING NEUROLOGICAL AND/OR PSYCHIATRIC DISORDERS

CROSS-REFERENCE TO RELATED APPLICATIONS

This application is a National Stage application under 35 U.S.C. § 371 of International Application No. PCT/EP2020/071525, filed on Jul. 30, 2020, which claims priority from GB1911024.6 entitled "COMPOUNDS FOR USE IN A METHOD OF TREATING OR PREVENTING NEUROLOGICAL AND/OR PSYCHIATRIC DISORDERS" filed Aug. 1, 2019, the contents of which are incorporated by reference in their entirety.

FIELD OF THE INVENTION

The present invention relates to compounds, namely ergoline derivatives, such as lysergic acid diethylamide, for use in a method of treating (alleviating the symptoms), preventing, reducing the symptoms of and/or slowing down the progression of a neurological and/or psychiatric disorder. In some aspects, the present invention relates to a method of treating, preventing, reducing the symptoms of and/or slowing down the progression of a neurological and/psychiatric disorder, which uses an ergoline derivative such as lysergic acid diethylamide or a pharmaceutically acceptable salt thereof.

BACKGROUND OF THE INVENTION

Normal aging is associated with a decline of cognitive abilities, such as learning capacity, processing speed, working memory, and executive functions (Glisky *Brain Aging: Models, Methods, and Mechanisms* D. R. Riddle Ed. 2007; Kirova et al. *Biomed. Res. Int.* 2015 748212). Upon aging, cells in the nervous system experience a number of changes including, for instance, increased amounts of oxidative stress, perturbated energy homeostasis, accumulation of damaged molecules e.g. aggregated proteins, lesions in nucleic acids etc. These changes can be exacerbated in vulnerable subjects, depending on genetic and environmental factors which determine the molecular and cellular mechanisms of aging. When cells fail to respond adaptively to age-related changes, neurological and/or psychiatric disorders can occur leading to pathological symptoms such as early and/or disproportionate decline in e.g. sensory, motor, and cognitive functions with time.

Recent studies have investigated how fundamental cellular and molecular changes occurring upon aging as well as genetic and environmental factors may render specific neuronal cells more prone to disease. Nonetheless, the pathological processes involved in the development of neurological and/or psychiatric disorders are poorly understood. Furthermore, there is currently no efficient treatment available for halting the progression of age-related diseases. To date only few treatments such as riluzole and memantine have been shown to slow disease progression in subjects suffering from amyotrophic lateral sclerosis (ALS) (Miller et al. *Amyotroph. Lateral Scler. Other Motor Neuron Disord.* 2003, 4, 191-206) or Alzheimer's disease (AD) (Reisberg et al. *Arch. Neurol.* 2006, 63, 49-54). There is hence an urgent need for novel therapies that can be used for effectively slowing and/or reversing age-related pathological processes, thus allowing the treatment and/or prevention of neurological and/or psychiatric disorders associated thereto.

Psychedelic substances such as mescaline, psilocybin, dimethyltryptamine (DMT) etc. have been used in traditional rites and therapy since ancient times, long before the Western world. Amongst these substances, (D)-lysergic acid diethylamide (LSD) is considered as a prototypical and reference psychedelic compound, which has been widely and successfully used by psychologists and psychiatrists in research and clinical practice until it became illegal in the mid-1960s. Recently, a considerable revival of interest has surrounded psychedelic substances including psilocybin, 5-methoxy-N,N-dimethyltryptamine (5-MeO-DMT), 2,5-dimethoxy-4-iodoamphetamine (DOI), LSD, 3,4-methylenedioxy-N-methamphatemine (MDMA), mescaline etc. in view of their considerable potential for brain research and therapy.

Clinical studies have investigated the use of psilocybin for treating depression, existential anxiety, and substance (tobacco, alcohol) addiction (Moreno et al. *J. Clin. Psychiatry* 2006, 67, 1735-1740; Grob et al. *Arch. Gen. Psychiatry* 2011, 68, 71-78; Johnson et al. *J. Psychopharmacology* 2014, 28, 983-992; Bogenschutz et al. *J. Psychopharmacology* 2015, 29, 289-299; Ross et al. *J. Psychopharmacology* 2016, 30, 1165-1180; Griffiths et al. *J. Psychopharmacology* 2016, 30, 1181-1197). Likewise, Ayahuasca, an entheogenic brew containing DMT in combination with monoamine oxidase inhibitors (MAOIs), has been investigated for treating major depressive disorder (Osorio Fde et al. *Rev. Bras. Psiquiatr.* 2015, 37, 13-20; Sanches et al. *J. Psychopharmacology* 2016, 36, 77-81). More recently, MDMA has evolved to "breakthrough therapy" for the treatment of post-traumatic stress disorder (PTSD) with FDA approval planned for 2021, whereas another hallucinogenic substance, ketamine, has been approved by the FDA for the treatment of resistant depression.

The potential of LSD for treating one of the most common and widely spread neurodegenerative disorder, Alzheimer's disease, has also been considered. WO 2016/145193 A1 proposes a method for treating Alzheimer's disease in a human subject comprising the administration of a pharmaceutical composition comprising LSD, or a pharmaceutically acceptable salt thereof, in an amount that is said to be sufficient for treating said Alzheimer's disease. The subjects targeted by the method of WO 2016/145193 A1 are elderly adults, e.g. typically adults with an age equal to or greater than 62 years, showing pathological symptoms of Alzheimer's disease such as frequent/persistent memory loss, coordination problems, aggression, inability to communicate etc. However, the method proposed in WO 2016/145193 A1 may have only limited efficacy.

In view of the foregoing, it is an object of the present invention to provide compounds for use in methods of treating, preventing, reducing the symptoms of and/or slowing the progression of a neurological and/or psychiatric disorder, in particular for treating or preventing a disease associated with a deficiency and/or decline of cognitive functions such as mild cognitive impairment or Alzheimer's disease. It is a further object of the present invention to provide pharmaceutical compositions comprising such compounds.

SUMMARY OF THE PRESENT INVENTION

The present invention provides a compound for use in a method of treating, preventing, reducing the symptoms of and/or slowing the progression of a neurological and/or psychiatric disorder comprising administering a compound to a subject and providing the subject with a cognitive training, e.g. concurrently, before and/or after administering the compound, wherein the compound is an ergoline derivative or a pharmaceutically acceptable salt thereof.

Specifically, the present inventors have surprisingly found that the administration of an ergoline derivative such as LSD in combination with a cognitive training can significantly enhance cognitive functions, in particular memory and learning capacity over a prolonged period, i.e. up to several days after administration, in rodents and humans. The present invention has been accomplished based on these findings.

The present invention thus relates to a compound for use in a method of treating, preventing, reducing the symptoms of or slowing the progression of a neurological and/or psychiatric disorder, wherein a therapeutically effective amount of a compound (i.e. an ergoline derivative such as LSD) is administered to a subject, and the subject is provided with a cognitive training, for instance a training of the spatial orientation, (visuospatial) memory and/or inductive reasoning.

The present invention in particular includes the following embodiments ("Items"):

1. Compound for use in a method of treating, preventing, reducing the symptoms of or slowing the progression of a neurological and/or psychiatric disorder,
   wherein a therapeutically effective amount of a compound is administered to a subject and the subject is provided with a cognitive training,
   wherein the compound is an ergoline derivative or a pharmaceutically acceptable salt thereof.
2. The compound for use according to item 1, wherein the compound is a lysergamide or a pharmaceutically acceptable salt thereof, preferably lysergic acid diethylamide (LSD) or a pharmaceutically acceptable salt thereof.
3. The compound for use according to item 1 or 2, wherein the compound is administered in
   (a) an amount of 2 to 20 µg per day, preferably 5 to 18 µg per day such as 15 µg per day, or
   (b) an amount of 20 to 150 µg per day, preferably 25 to 125 µg per day such as 75 µg per day or 100 µg per day.
4. The compound for use according to any of items 1 to 3 wherein the cognitive training comprises or consists of training spatial orientation tasks, spatial memory tasks and/or inductive reasoning tasks, preferably spatial orientation tasks and/or inductive reasoning tasks, more preferably the cognitive training consists of training inductive reasoning tasks.
5. The compound for use according to any of items 1 to 4, wherein the compound is administered in (a) an amount of 2 to 20 µg per day every 1 to 6 days over a period of up to 600 days.
6. The compound for use according to item 5, wherein the cognitive training is provided once to three times a day concurrently with, before and/or after the administration of the compound to the subject, preferably once to three times a day concurrently with the administration of the compound.
7. The compound for use according to any of items 1 to 4, wherein the compound is administered in (b) an amount of 20 to 150 µg per day every 1 to 6 days over a period of up to 60 days.
8. The compound for use according to item 7, wherein the cognitive training is provided once to three times a day concurrently with, before and/or after the administration of the compound, preferably once to three times a day after the administration of the compound.
9. The compound for use according to any of items 1 to 8, wherein the neurological disorder is selected from dementia, mild cognitive impairment (MCI), Alzheimer's disease, frontotemporal degeneration, Lew body disease, Parkinson's disease, vascular dementia, prion disease, Huntington's disease, dementia/neurocognitive issues due to a HIV infection, post-operative cognitive decline, post-operative dementia, multiple sclerosis, amyotrophic lateral sclerosis (ALS), spinocerebellar ataxia (SCA), neuronal ceroid lipofuscinosis (NCL), chronic fatigue syndrome, brain injury, central and/or peripheral neuropathy and stroke; and the psychiatric disorder is selected from anxiety, disorders of the obsessive compulsive spectrum such as mania or body dysmorphic disorder, phobias, substance addiction such as alcohol addition, opioid addiction and benzodiazepine addiction, behavioral addictions such as gambling, binge eating disorder, premenstrual dystrophic disorder, seasonal effective disorder, adjustment disorder, bipolar disorder and borderline personality disorder.
10. The compound for use according to any of items 1 to 9, wherein the neurological disorder is selected from MCI and Alzheimer's disease, preferably MCI.
11. The compound for use according to any of items 1 to 10, wherein the subject is a human subject, preferably a middle-aged adult or an older adult, more preferably an older adult.
12. The compound for use according to any of items 1 to 11, wherein the subject has a score of from 10 to 26 points, preferably of from 12 to 24 points, more preferably of from 18 to 23 such as about 22, in a Montreal Cognitive Assessment (MoCA).
13. Composition for use in a method of treating, preventing, reducing the symptoms of or slowing the progression of a neurological and/or psychiatric disorder,
    wherein the composition is administered to a subject and the subject is provided with a cognitive training, and
    wherein the composition comprises a compound as defined in item 1 or item 2 and one or more components selected from a carrier, a diluent and other excipients.
14. The compound for use according to any of items 1 to 12 or the composition for use according to item 13, wherein the compound or the composition is administered concurrently with, before or after one or more therapeutic agents such as an acetylcholinesterase inhibitor, an NMDA receptor inhibitor, an antidepressant, an anxiolytic, a cannabinoid; or therapies such as transcranial magnetic stimulation (TMS), electroconvulsive therapy, deep brain stimulation, behavioral therapies such as mindfulness, acceptance and commitment therapy, cognitive behavioral therapy (CBT), biofeedback, and hypnosis.
15. Method for treating, preventing, reducing the symptoms of or slowing the progression of a neurological and/or psychiatric disorder, wherein a therapeutically effective amount of a compound is administered to a subject in need thereof and the subject is provided with a cognitive training, wherein the compound is an ergoline derivative or a pharmaceutically acceptable salt thereof, preferably LSD or a pharmaceutically acceptable salt thereof.

FIGURES

FIG. 1—Effects of LSD on novel object preference in rats. (A) Experimental design of the novel object preference test in rats. The animals were treated with LSD or saline, and subsequently tested for novel object preference several days later. (B) Novel object preference test. The animals were individually placed in an experiment arena containing two objects and trained for 7 minutes. The animals were removed from the arena and allowed to rest for 30 minutes. In the meantime, one of the objects was replaced by a new object. The animals were individually placed in the experiment arena for 3 minutes, and their preference for the novel object was evaluated by determining the time spent by the respective animals to explore the novel object.

Figure 2:
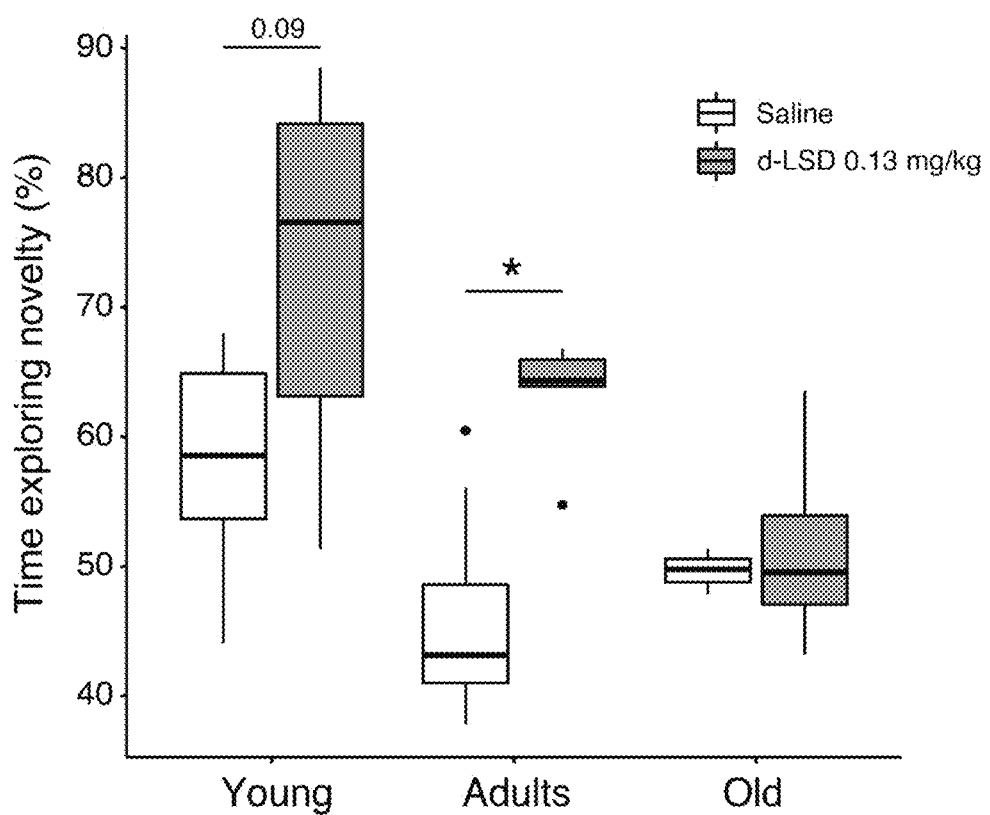

FIG. 2—Results of the novel object preference test in rats of different ages. The novel object preference was significantly increased in young and adult animals.

Figure 3:
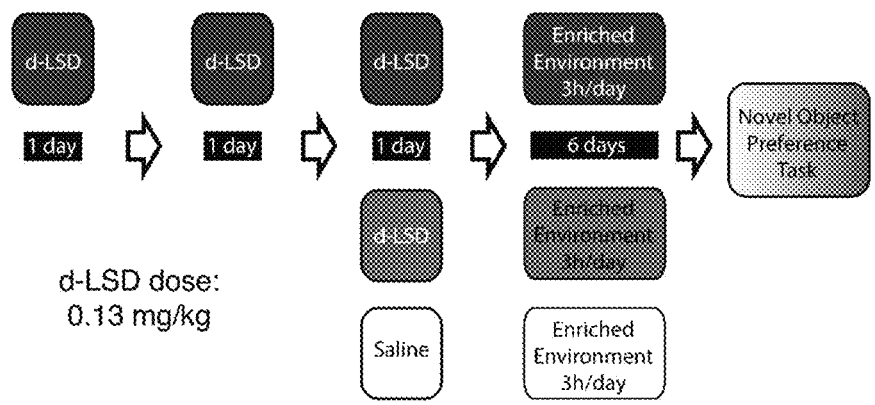
Figure 3:
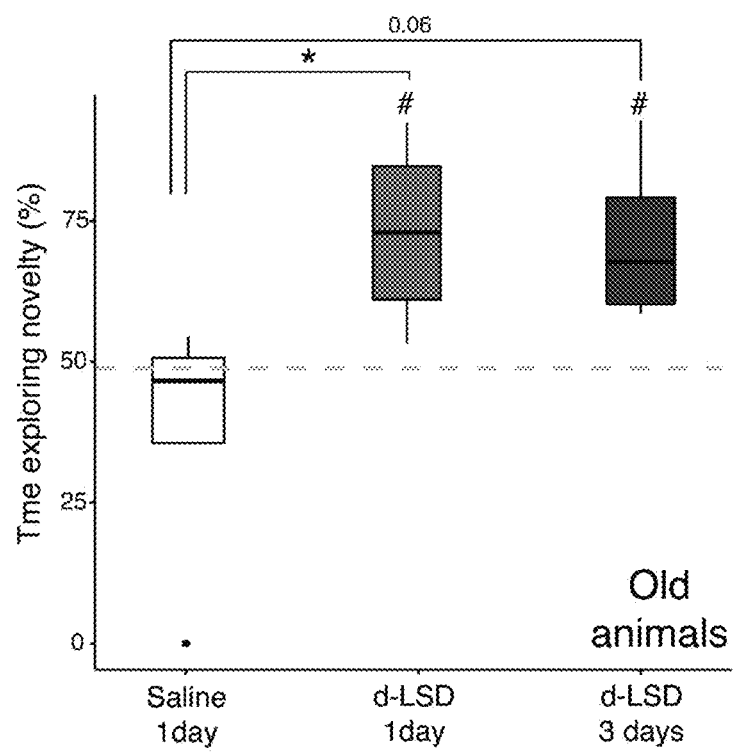

FIG. 3—Effects of LSD and enriched environment on novel object preference in rats. (A) Experimental design of the enriched environment test in old animals. Old animals were administered with saline (control group) or 0.13 mg/kg of test compound (LSD) for 1 day or 3 consecutive days, followed by exposure to an enriched environment for 6 consecutive days (3 hours per day). (B) Results. The administration of LSD in combination with an enriched environment led to a significant enhancement of cognitive functions as compared to the control group.

Figure 4:
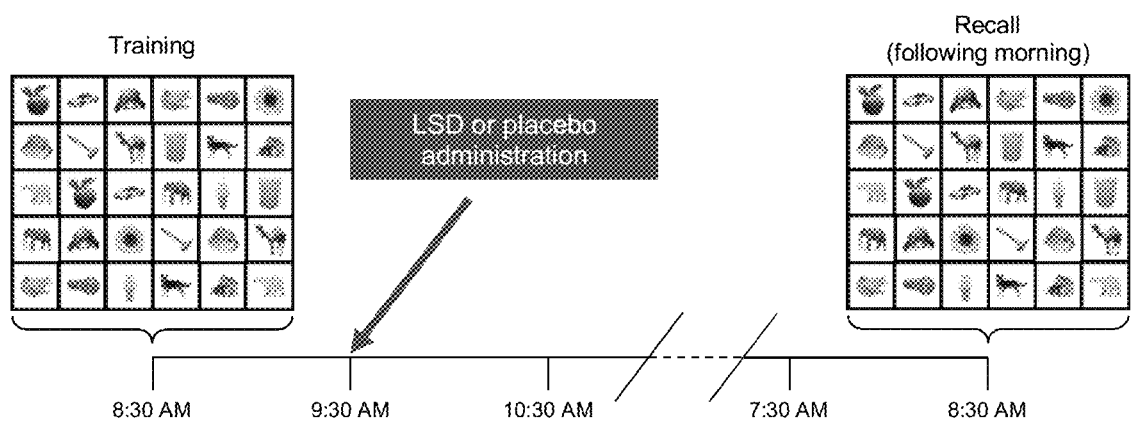
Figure 4:
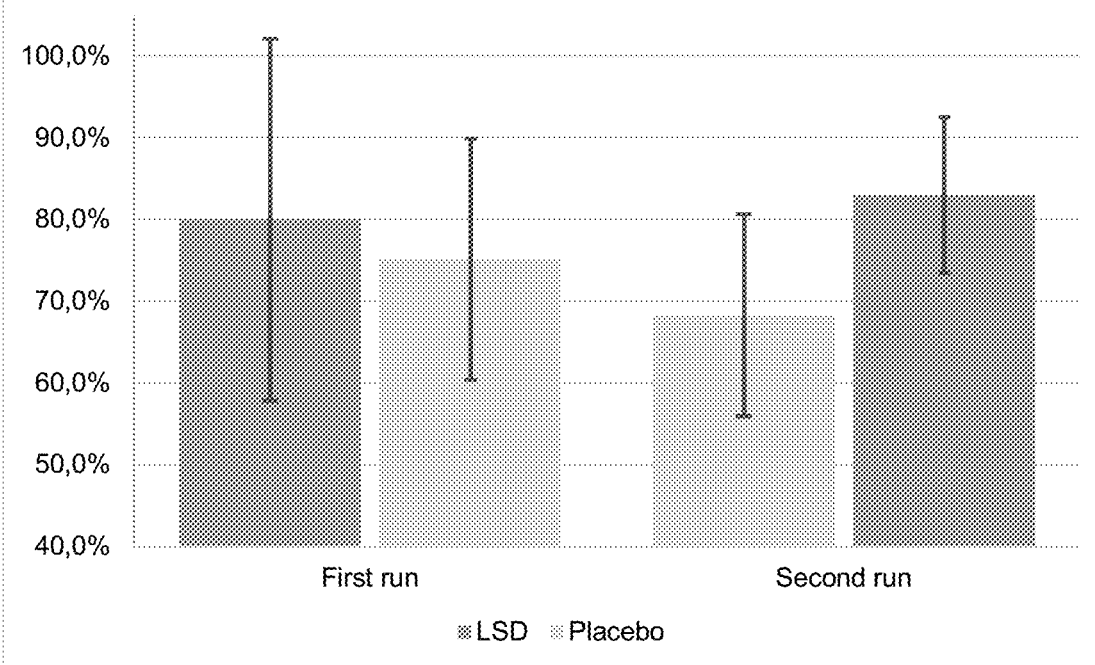

FIG. 4—Effects of LSD on learning and memory in humans. (A) Experimental design of the two-dimensional visuospatial location (memory) task. (B) Results. The performance of the tested subjects in the visuospatial location task was significantly improved when administered with a single dose of LSD as compared to placebo.

Figure 5:
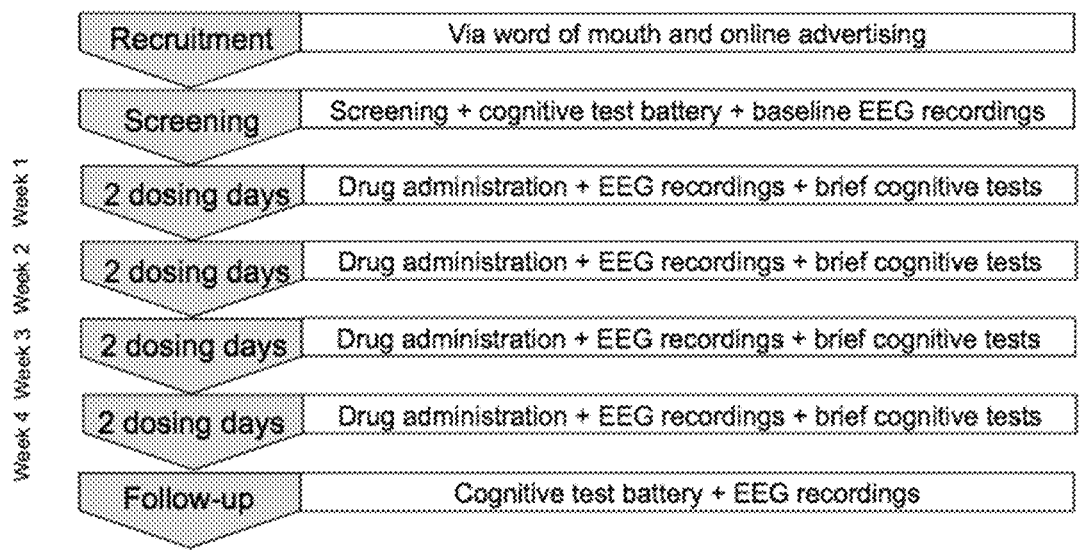

FIG. 5—Effects of prolonged LSD administration on mood and cognitive functions in humans. Study timeline.

Figure 6:
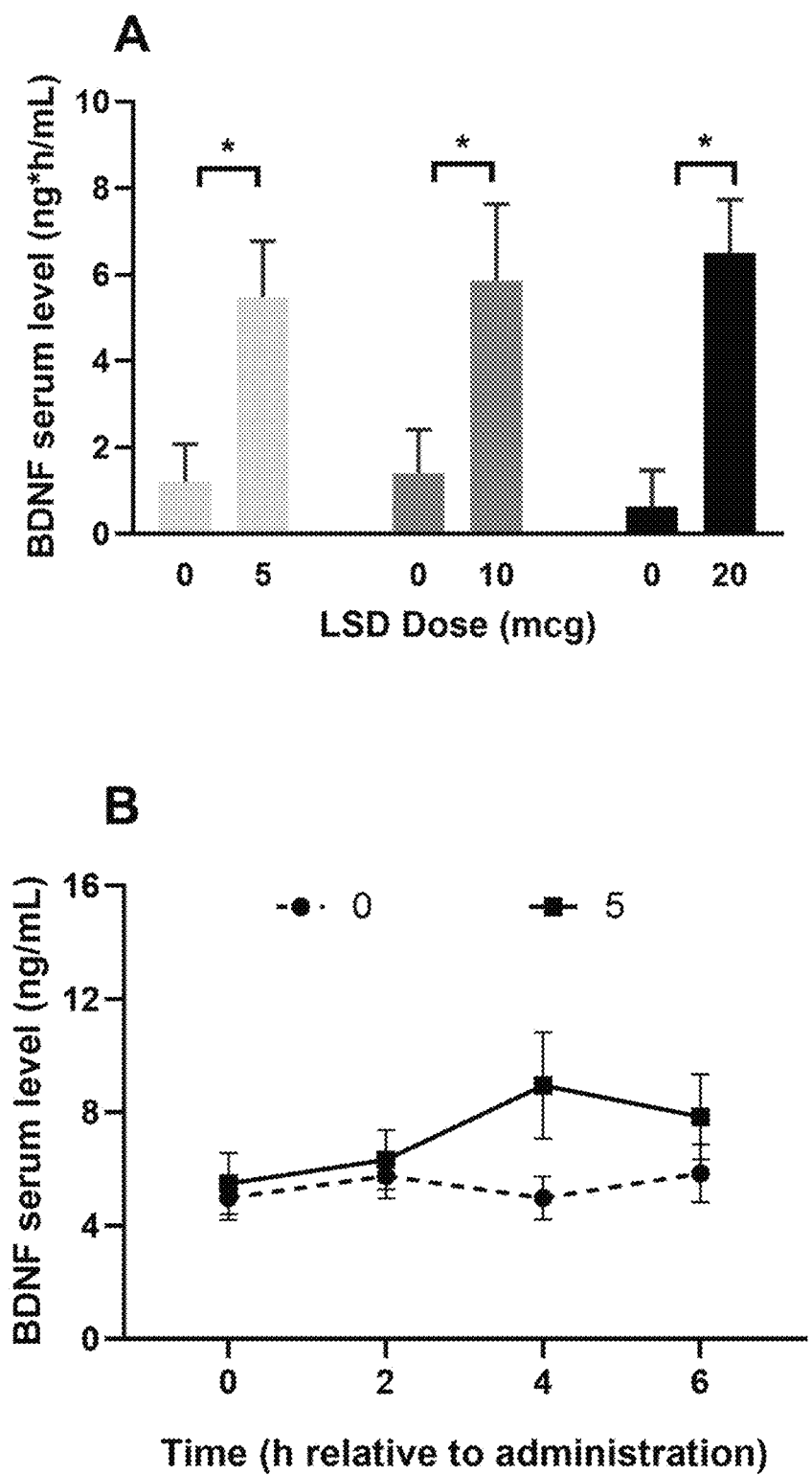
Figure 6:
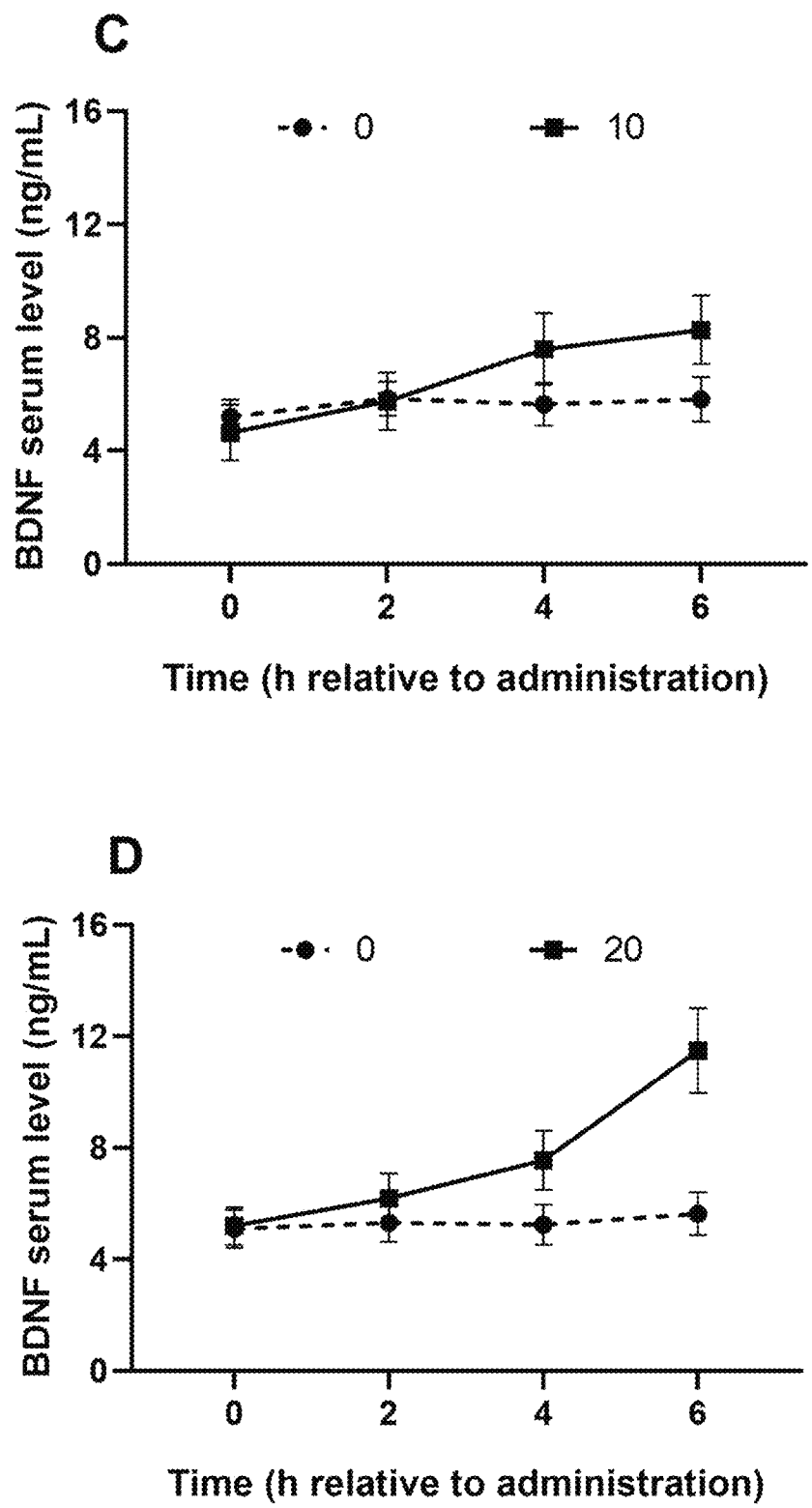

FIG. 6—Effects of LSD administration on brain-derived neurotrophic factor (BDNF) levels. Results: (A) Total mean AUC of BDNF serum levels for all complete within-subject (WS) LSD-placebo cases. (B)-(D) BDNF serum levels for each dose with the corresponding WS placebo condition per time of testing.

DETAILED DESCRIPTION OF THE PRESENT INVENTION

1. Definitions

The term "neurological disorder" as used herein means any disorder of the nervous system. Examples of neurological disorders include dementia, mild cognitive impairment (MCI), frontotemporal degeneration, Lew body disease, Parkinson's disease, vascular dementia, prion disease, Huntington's disease, dementia/neurocognitive issues due to a HIV infection, post-operative cognitive decline, post-operative dementia, multiple sclerosis, amyotrophic lateral sclerosis (ALS), spinocerebellar ataxia (SCA), neuronal ceroid lipofuscinosis (NCL) such as Batten disease, chronic fatigue syndrome, brain injury, central and/or peripheral neuropathy, stroke.

The term "psychiatric disorder" (sometimes called "mental illness") as used herein means a behavioral or mental pattern that causes significant distress or impairment of personal functioning. Examples of psychiatric disorders include anxiety, disorders of the obsessive-compulsive spectrum, phobias, substance addiction, behavioral addictions, premenstrual dystrophic disorder, seasonal effective disorder, adjustment disorder, bipolar disorder, borderline personality disorder, functional pain syndrome.

The terms "treating" (or "treatment") or "preventing" (or "prevention") as used herein, unless otherwise indicated by context, refer to therapeutic or prophylactic treatment wherein the object is to inhibit, prevent, reduce or alleviate an undesired physiological change or disorder, such as the progression and/or symptoms of a neurological and/or psychiatric disorder. As to the present invention, beneficial or desired clinical results include e.g. alleviation of symptoms, diminishment of extent of disease, stabilized (i.e. not worsening) state of disease, delay or slowing of disease progression, amelioration or palliation of the disease state, and remission (whether partial or total). Subjects in need of treatment or preventive treatment include those already with the disorder as well as those prone to have or develop the disorder e.g. due to genetic predisposition and/or family background.

Diagnostic tests for determining the symptoms, progression and/or state of disease are well-established in the art and known to the skilled person (e.g. the physician). For instance, the progression and state of MCI or Alzheimer's disease in a subject (patient) can be determined by relying on well-established diagnostic tests including e.g. neuropsychological tests such as the Montreal Cognitive Assessment (MoCA) or the Mini-Mental State Examination (MMSE, "Folstein" test), neurological examination and/or psychological tests such as tests for depression in Alzheimer's disease.

The term "therapeutically effective amount" as used herein refers to an amount of a compound (e.g. LSD) effective to treat, prevent, reduce the symptoms or slow down the progression of a neurological and/or psychiatric disorder when used in combination with a cognitive training. The therapeutically effective amount of the compound leads to one or more of the aforementioned beneficial or desired clinical results. In one aspect of the present invention, the therapeutically effective amount leads to one or more of the aforementioned beneficial or desired clinical results, without substantially inducing the physical and/or psychological effects of ergoline derivative (sometimes referred to as "microdosing").

The term "derivative" as used herein is meant to encompass the chemical modification of a compound. Examples of such modifications include the replacement of a hydrogen by a halo group, an alkyl group, an acyl group etc. Furthermore, the term "ergoline derivative" refers to a class of compounds structurally related to the naturally occurring compound ergoline. The whole class of ergoline-structurally related compounds is sometimes simply referred to as "ergolines".

Ergolines are tetracyclic molecules, ultimately derived from alkaloids produced by the ergot fungus *Clavipeps purpurea*. A great number of (semi)synthetic and naturally occurring ergoline derivatives have been discovered and studied. These substances are known to exhibit agonist activity at the 5-hydroxytryptamine (5-$HT_{2A}$) receptor which, in the brain, plays an essential role in regulation of the cortical function and cognition. Amongst them, LSD, the diethylamide-derivative of (D)-lysergic acid reportedly constitutes one of the most potent psychedelic substances in humans. For instance, a moderate dose of LSD (e.g. 75 to 150 μg p.o.) gives rise to significantly altered states of consciousness, sometimes accompanied with e.g. euphoria, hallucinations, alterations of thinking etc. (Passie et al. *CNS Neur. & Ther.* 2008, 14, 295-314).

In some aspects of the present invention, the ergoline derivative may be lysergic acid or a lysergamide, i.e. an amide derivative of lysergic acid, preferably a compound satisfying the following formula:

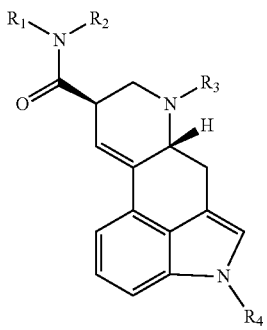

wherein $R_1$ and $R_2$ each independently represent an alkyl group having 1 to 6 carbon atoms which may be substituted, an alkene group having 1 to 6 carbon atoms which may be substituted, or an alkyne group having 1 to 6 carbon atoms which may be substituted, and $R_1$ and $R_2$ may be linked to each other to form a ring; $R_3$ is an alkyl group having 1 to 4 carbon atoms which may be substituted, an alkene group having 1 to 4 carbon atoms which may be substituted, or an alkyne group having 1 to 4 carbon atoms which may be substituted; and $R_4$ is a hydrogen atom, an alkyl group having 1 to 4 carbon atoms, or a carbonyl-containing group having 1 to 4 carbon atoms.

Examples of ergoline derivatives include lysergic acid 2-butyl amide, lysergic acid 2-pentyl amide, lysergic acid 3-pentyl amide, lysergic acid 2-hexyl amide, N,N-diallyl lysergamide, lysergic acid methylisopropyl amide, lysergic acid diethylamide (LSD), 6-ethyl-6-nor-lysergic acid diethylamide, 6-propynyl-6-nor-lysergic acid diethylamide, 6-allyl-6-nor-lysergic acid diethylamide, 6-propyl-6-nor-lysergic acid diethylamide, 6-cyclopropyl-6-nor-lysergic acid diethylamide, 6-butyl-6-nor-lysergic acid diethylamide, 1-acetyl lysergic acid diethylamide, 1-propyonyl lysergic acid diethylamide, 1-propyonyl-6-ethyl-6-nor-lysergic acid diethylamide, N-morpholinyl lysergamide, N-pyrrolidyl lysergamide, N-piperidyl lysergamide, and lysergic acid 2,4-dimethylazetidine.

The expression "pharmaceutically acceptable salts" as used herein refers to derivatives of the disclosed compounds wherein the parent compound is modified by making acid or base salts thereof. The pharmaceutically acceptable salts include the conventional non-toxic salts or the quaternary ammonium salts of the parent compound formed, for example, from non-toxic inorganic or organic acids. Lists of suitable salts can be found in *Remington's Pharmaceutical Sciences*, $17_{th}$ ed., Mack Publishing Company, Easton, PA, 1985, page 1418, S. M. Berge, L. M. Bighley, and D. C. Monkhouse, "Pharmaceutical Salts," J. Pharm. Sci. 66 (1), 1-19 (1977); P. H. Stahl and C. G. Wermuth, editors, Handbook of Pharmaceutical Salts: Properties, Selection and Use, Weinheim/Zürich, Wiley-VCH, 2008 and in A. K. Bansal et al., Pharmaceutical Technology, 3(32), 2008. The pharmaceutical salts can be synthesized from the parent compound which contains a basic or acidic moiety by conventional chemical methods. Preferably, the pharmaceutical acceptable salt is a tartrate salt.

Unless specified otherwise, chiral compounds may be present in the form of a pure stereoisomer or in the form of a mixture of stereoisomers, including the 50:50 racemate. In the context of the present invention, references to specific stereoisomers are to be understood as references to compounds, wherein the designated stereoisomer is present in at least 90% enantiomeric excess (ee), more preferably at least 95% ee and most preferably 100% ee.

The expression "cognitive training" (or "brain training") as used herein refers to a program of regular mental activities (e.g. involving one or more tasks) intended to maintain or improve the subject's cognitive abilities (functions). For instance, cognitive training in a human subject may involve training one or more tasks selected from criterion tasks, near-transfer and/or far transfer tasks, updating tasks, span tasks, knowledge tasks such as language tasks, spatial orientation tasks, inductive reasoning tasks and spatial memory tasks. Cognitive training in animals may involve provide the animal (e.g. a rodent) with an "enriched" environment that stimulates the brain (e.g. flexibility, curiosity, memory skills) by its physical and social surroundings.

The expression "spatial orientation" as used herein refers to the ability to identify the position or direction of objects or points in space. Spatial orientation can be trained and assessed by conducting specific tasks known to the person skilled in the art e.g. by asking a subject (patient) to perform spatial transformations such as rotations or inversions of stimuli as described further below.

The expression "inductive reasoning" as used herein refers to the ability to use a series of specific observations (sometimes called "evidence") to support the probability of a more general conclusion. Inductive reasoning can be trained and assessed by conducting specific tasks known to the person skilled in the art and described further below.

The expression "spatial memory" as used herein refers to the ability to record information about one's environment. Spatial memory can be trained and assessed by conducting specific tasks known to the person skilled in the art e.g. by asking a subject to perform visuospatial location tasks as described further below.

The expressions "young adult", "middle-aged adult" and "older adult" as used herein refer to the human age ranges of from 18 to 39 years old, 40 to 59 years old (in particular 40 to 49 years old), and equal to or greater than 60 years old, respectively.

Where the present description refers to "preferred" embodiments/features, combinations of these "preferred" embodiments/features shall also be deemed as disclosed as long as this combination of "preferred" embodiments/features is technically meaningful.

Hereinafter, in the present description of the invention and the claims, the use of the terms "containing" and "comprising" is to be understood such that additional unmentioned elements may be present in addition to the mentioned elements.

However, these terms should also be understood as disclosing, as a more restricted embodiment, the term "consisting of" as well, such that no additional unmentioned elements may be present, if this is technically meaningful.

2. Overview

The present invention is based on the finding that the administration of an ergoline derivative such as LSD or a pharmaceutical salt thereof in combination with a cognitive training can significantly enhance cognitive functions, especially memory and learning capacity, in a subject. It is hence expected that the compound of the present invention can be suitably and successfully used in a method of treating, preventing, reducing the symptoms of and/or slowing the progression of neurological and/or psychiatric disorders, especially disorders associated with a deficiency and/or decline of cognitive functions.

Without being bound to any theory, it is believed that the administration of an ergoline derivative can increase the expression levels of synaptophysin in (human) neuronal cells, thereby stimulating cell growth and synapse formation, and that performing a cognitive training (concurrently with, before and/or after administration of the ergoline derivative) allows magnifying these effects and also making these effects persistent over a prolonged period of time. As a result, the administration of an ergoline derivative combined with a cognitive training can (synergistically) improve cognitive functions and also reverse pathological processes associated with a deficit and/or decline of cognitive functions.

3. Compound

The compound of the present invention is an ergoline derivative or a pharmaceutically acceptable salt thereof. The compound used herein (e.g. LSD) exhibits a high efficacy at low doses as well as a low toxicity. Therefore, the compound of the present invention is advantageous is terms of efficacy and toxicity (adverse effects) over other psychedelic compounds such as DMT or mescaline.

According to one embodiment, the ergoline derivative is lysergic acid or a lysergamide, i.e. an amide derivative of lysergic acid, preferably a compound satisfying the following formula:

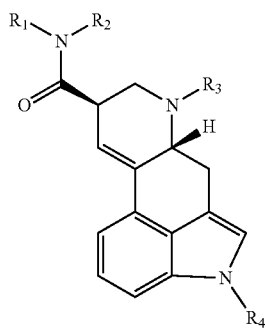

wherein $R_1$ and $R_2$ each independently represent an alkyl group having 1 to 6 carbon atoms which may be substituted, an alkene group having 1 to 6 carbon atoms which may be substituted, or an alkyne group having 1 to 6 carbon atoms which may be substituted, and $R_1$ and $R_2$ may be linked to each other to form a ring; $R_3$ is an alkyl group having 1 to 4 carbon atoms which may be substituted, an alkene group having 1 to 4 carbon atoms which may be substituted, or an alkyne group having 1 to 4 carbon atoms which may be substituted; and $R_4$ is a hydrogen atom, an alkyl group having 1 to 4 carbon atoms, or a carbonyl-containing group having 1 to 4 carbon atoms; or a pharmaceutically acceptable salt thereof.

According to one embodiment, the ergoline derivative is selected from lysergic acid 2-butyl amide, lysergic acid 2-pentyl amide, lysergic acid 3-pentyl amide, lysergic acid 2-hexyl amide, N,N-diallyl lysergamide, lysergic acid methylisopropyl amide, lysergic acid diethylamide (LSD), 6-ethyl-6-nor-lysergic acid diethylamide, 6-propynyl-6-nor-lysergic acid diethylamide, 6-allyl-6-nor-lysergic acid diethylamide, 6-propyl-6-nor-lysergic acid diethylamide, 6-cyclopropyl-6-nor-lysergic acid diethylamide, 6-butyl-6-nor-lysergic acid diethylamide, 1-acetyl lysergic acid diethylamide, 1-propyonyl lysergic acid diethylamide, 1-propyonyl-6-ethyl-6-nor-lysergic acid diethylamide, N-morpholinyl lysergamide, N-pyrrolidyl lysergamide, N-piperidyl lysergamide, lysergic acid 2,4-dimethylazetidine, and pharmaceutically acceptable salts thereof.

According to one preferred embodiment, the ergoline derivative is (D)-lysergic acid diethylamide (LSD) or a pharmaceutically acceptable salt thereof.

4. Cognitive Training

The compound of the present invention is administered to a subject (patient) in combination with a cognitive training, which involves performing on a regular basis (once to 10 times a day) one or more tasks such as criterion tasks, near-transfer and/or far transfer tasks, updating tasks, span tasks, knowledge tasks such as language tasks, spatial orientation tasks, inductive reasoning tasks and spatial memory tasks. Cognitive training tasks such as criterion tasks, near-transfer and/or far transfer tasks, updating tasks, span tasks and knowledge tasks are known to the person skilled in the art and have been described e.g. by Strobach et al. in *Journal of Cognitive Enhancement* 2017, 1, 539-558.

According to one preferred embodiment, the cognitive training comprises or consists of training spatial orientation tasks, spatial memory tasks and/or inductive reasoning tasks, preferably comprises or consists of spatial orientation tasks and/or inductive reasoning tasks. More preferably, the cognitive training consists of training inductive reasoning tasks.

Spatial orientation can be assessed by four measures. Three of the tests (Primary Mental Abilities (PMA) Space, Object Rotation, and Alphanumeric Rotation) are multiple response measures of 2D mental rotation ability. The subject is shown a model line drawing and asked to identify which of 6 choices shows the model drawn in different spatial orientations. There are two or three correct responses possible for each test item. The Object Rotation test and the Alphanumeric test are constructed such that the angle of rotation in each answer is identical with the angle used in the PMA Space test. The three tests vary in item content. Stimuli for the PMA test are abstract figures, the Object Rotation test involves drawings of familiar objects, and the Alphanumeric test contains letters and numbers. The fourth test, Cube Comparisons assesses mental rotation in 3D space.

Inductive reasoning can be assessed by four measures. The PMA reasoning measure assesses inductive reasoning ability using letter series problems. The subject is shown a series of letters and must select the next letter in the series from five letter choices. The Adult Development and Enrichment Project Letter Series test also contains letter series problems; however, some of the problems involve pattern-description rules other than those found in the PMA measure. The Word Series test parallels the PMA measure in that the same pattern-description rule is used for each item. However, the test stimuli are days of the week or months of the year, rather than letters, and involves different types of pattern-description rules involving mathematical computations. The PMA Spatial Orientation and Reasoning tests were administered at previous SLS measurement points, and thus provide the most direct assessment of training improvement and remediation.

According to one embodiment, the cognitive training is provided once to 10 times a day, preferably 1 to 3 times a day e.g. once a day, concurrently with, before or after the administration of the compound. In some instances, said cognitive training can be provided every 1 to 7 days, preferably every 1 to 3 days, and more preferably every day, e.g. the cognitive training may be provided 1 to 3 times a day every 1 to 3 days or every day.

5. Composition

The compounds of the present invention can be provided in the form of pharmaceutical compositions for human or animal usage in human and veterinary medicine. Such compositions typically comprise a therapeutically effective amount of ergoline derivative according to the present invention or a pharmaceutically acceptable salt thereof, and one or more components selected from a carrier, a diluent and other excipients.

Suitable carriers, diluents and other excipients for use in pharmaceutical compositions are well known in the art, and are for instance described in Remington's Pharmaceutical Sciences, Mack Publishing Co. (Gennaro AR, 1985). The carrier, diluent and/or other excipient can be selected with regard to the intended route of administration and pharmaceutical practice. The pharmaceutical compositions can comprise as the carrier, diluents and/or other excipients, or in addition to, any suitable binder(s), lubricant(s), suspending agent(s), coating agent(s), solubilizing agent(s).

6. Use of Ergoline Derivative or Composition Thereof in Methods of Preventing or Treating Neurological and/or Psychiatric Disorders The compounds of the present invention can be used to treat or prevent a neurological and/or psychiatric disorder. The treatment can be a therapeutic and/or prophylactic treatment, with the aim being to reverse, prevent, reduce or stop an undesired physiological change or disorder. In some aspects, the treatment can prolong survival of a subject as compared to expected survival if not receiving the treatment.

The disease that is treated by the compound can be any neurological and/or psychiatric disease that benefits from the treatment, including chronic and acute disorders or diseases and also those pathological conditions which predispose to the disorder. In some aspects, the neurological disorder is selected from dementia, mild cognitive impairment (MCI), Alzheimer's disease, frontotemporal degeneration, Lew body disease, Parkinson's disease, vascular dementia, prion disease, Huntington's disease, dementia/neurocognitive issues due to a HIV infection, post-operative cognitive decline, post-operative dementia, multiple sclerosis, amyotrophic lateral sclerosis (ALS), spinocerebellar ataxia (SCA), neuronal ceroid lipofuscinosis (NCL), chronic fatigue syndrome, brain injury, central and/or peripheral neuropathy, and stroke; and the psychiatric disorder is selected from anxiety, disorders of the obsessive compulsive spectrum such as mania or body dysmorphic disorder, phobias, substance addiction such as alcohol addition, opioid addiction and benzodiazepine addiction, behavioral addictions such as gambling, binge eating disorder, premenstrual dystrophic disorder, seasonal effective disorder, adjustment disorder, bipolar disorder and borderline personality disorder. According to one embodiment, the neurological and/or psychiatric disorder is not Alzheimer's disease.

According to one preferred embodiment, the compound of the present invention can be in a method of treatment or prevention of a psychiatric and/or neurological disorder selected from MCI and Alzheimer's disease, preferably MCI.

According to one preferred embodiment, the subject is a human subject, preferably a middle-aged adult or an older adult, more preferably an older adult (i.e. an adult with an age equal to or greater than 60 years old).

In one aspect, the severity and state of disease can be determined prior to initiation of the therapeutic regimen and/or during the therapy. For instance, the subject may have a score of from 10 to 26 points, preferably of from 12 to 24 points, more preferably of from 18 to 23 such as about 22, in a Montreal Cognitive Assessment (MoCA). When treating MCI or Alzheimer's disease, the therapeutic effect that is observed can be an improvement of cognitive functions as reflected by an increase of the MoCA score.

According to one embodiment, the present invention relates to a compound for use in a method of treating, preventing, reducing the symptoms of or slowing the progression of a neurological and/or psychiatric disorder, wherein a therapeutically effective amount of a compound is administered to a subject, wherein the compound is an ergoline derivative or a pharmaceutically acceptable salt thereof, preferably LSD or a pharmaceutically acceptable salt thereof, and wherein the neurological and/or psychiatric disorder is not Alzheimer's disease. According to this embodiment, the subject is preferably a young or a middle-aged adult (e.g. an adult with an age ranging from 18 to 49 years old), more preferably a young or middle-aged adult having a MoCA score ranging from 18 to 26 e.g. about 23. Preferably, the disease that is treated by the compound is NCL or MCI, more preferably MCI.

The routes for administration (delivery) include one or more of oral (e.g. tablet, capsule, ingestable solution), topical, mucosal (e.g. nasal spray, aerosol for inhalation), nasal, parenteral (e.g. an injectable form), and sublingual. According to a preferred embodiment, the compound of the present invention is administered orally or sublingually.

In the present invention, a therapeutically effective amount of ergoline derivative is administered to a subject in combination with a cognitive training as described above.

According to one preferred embodiment, the compound of the present invention is administered in (a) an amount of 2 to 20 µg per day, preferably 4 to 18 µg per day, more preferably 5 to 17 µg per day, and most preferably 6 to 16 µg per day, in particular about 15 µg per day. The compound is preferably administered once (daily) every 1 to 6 days, preferably once every 1 to 5 days, more preferably once every 1 to 3 days, over a period of up to 600 days, preferably over a period of up to 180 days, more preferably over a period of up to 30 days. In one embodiment, the compound is administered once every day over a period of up to 60 days. The cognitive training is preferably provided once to three times a day concurrently with, before or after the administration of the compound to the subject, more preferably once to three times a day, e.g. once a day, concurrently with the aforementioned administration of the compound.

According to another preferred embodiment, the compound of the present invention is administered in (b) an amount of 20 to 150 µg per day, preferably 25 to 125 µg per day, more preferably 30 to 100 µg per day, and most preferably 40 to 75 µg per day, in particular about 50 µg per day. The compound is preferably administered once (daily) every 1 to 6 days, preferably once every 1 to 5 days, more preferably once every 1 to 3 days, over a period of up to 60 days, preferably over a period of up to 30 days, more preferably over a period of up to 20 days. The cognitive training is preferably provided once to three times a day concurrently with, before or after the administration of the compound, more preferably once to three times a day after the administration of the compound.

In some aspects, the therapeutically effective amount can be determined by a physician on a routine basis. The specific dose level and frequency of dosage for any particular subject/patient can vary and depends on a variety of factors including the activity of the specific drug compound employed, the metabolic stability and length of action of that compound, the patient's age, body weight, general health, sex, diet, mode and time of administration, rate of excretion, drug combination, the severity of the particular condition, and the individual undergoing therapy. These factors are taken into account by the physician when determining the therapeutically effective dose.

7. EXAMPLES

In the following examples, (d)-LSD (in the following simply "LSD") dissolved in distilled water was used as the test compound. The test compound as used herein can be prepared relying on procedures and methodologies which are well-known to the person skilled in the art, e.g. on the procedure described in patent document U.S. Pat. No. 2,736,728. The test compound used in the following examples had a purity of more than 99.8% as determined by high-performance liquid chromatography (HPLC).

7.1 Example 1: Effects of LSD on Novel Object Preference in Rats

The effects of the test compound on cognitive functions in rodents, in particular on memory and learning capacity, were investigated using a novel object preference test (sometimes called "novel object recognition task") according to the experimental design depicted in FIG. 1A. More specifically, the novel object preference test was carried out as follows:

Wistar Rats (outbred albino rats; Janvier Labs) sorted in different age groups, i.e. young (about 2 months), adult (about 9 months) and old (about 12-18 months), were administered with a saline solution (sodium chloride; 0.9% in water) or an aqueous solution of the test compound (LSD) by intraperitoneal injection (dose: 0.13 mg/kg).

Before the injection the animals were housed with other animals, and after the injection of the saline or test compound the animals were housed individually. For ten hours following the administration, the animals were video-recorded and stayed alone during the acute effects of the test compound (or saline). Then, the animals were allowed to recover for a period of 3 or 9 days.

After recovery, the animals were individually placed in an experiment arena (45×45×45 cm) once a day for 10 minutes over a period of 3 days (acclimatization session). The experiment arena as used herein typically includes two 3D printed bases located on the arena's floor 10 cm apart from each other, which are intended for mounting and fixing the test objects. However, said bases are empty during the acclimatization session.

Then, the 3D printed bases were mounted with the same number (i.e. 2) and type of objects (identical LEGO™ pieces each having 12 edges and 12 vertices). The animals were individually placed in the experiment arena and trained for 7 minutes (training session). At the onset of the training session, the animals were individually placed facing the same wall of the arena, with their backs to the objects.

The animals were removed from the arena and allowed to rest for 30 minutes. In the meantime, one of the objects was replaced by a new object having the same dimensions (height and base) as the previous object but a different shape (LEGO™ piece, 14 edges and 14 vertices). The animals were individually placed in the experiment arena for 3 minutes, and their preference for the novel object was evaluated by determining the time spent by the respective animals to explore the novel object (test session; FIG. 1B). At the onset of the test, the animals were individually placed facing the same wall of the arena, with their backs to the objects in a similar manner as during the training session.

The results are shown in FIG. 2. Particularly it can be seen that the novel object preference was significantly increased in young animals, i.e. the preference was increased from a baseline level of about 60% (saline/pre-treatment) to about 80% (LSD-administered/post-treatment). Likewise a significant increase of the novel object preference was observed in adult animals, i.e. the preference was increased from about 40% (saline/pre-treatment) to about 60% (LSD-administered/post-treatment). In old animals, the novel object preference was not significant.

Overall, these results demonstrate that the compound of the present invention can significantly enhance cognitive functions of young and adult animals, e.g. memory and learning capacity, over a prolonged period of time, i.e. up to several days after administration. However, an enhancement of cognitive functions was not observed in respect of old animals.

7.2 Example 2: Effects of LSD and Cognitive Training on Novel Object Preference in Rats The potential of the test compound combined with a cognitive training to rescue cognitive functions (called "enriched environment") was evaluated in old animals according to the experimental design depicted in FIG. 3A. More specifically, the enriched environment test was carried out as follows:

Old animal (about 12-18 months) were administered with saline (control group) or 0.13 mg/kg of test compound (LSD) for 1 day or 3 consecutive days, followed by exposure to an enriched environment for 6 consecutive days (3 hours each day). The enriched environment used herein typically consists of card boxes with 8 different rooms, wherein it is possible to find a variety of objects such as PVC tubes, toilet paper cardboard tubes or wood objects so as to stimulate the exploratory behavior. The animals were allowed to explore the enriched environment freely in groups of 3 to 5 animals. The effects of the test compound followed by the enriched environment were analyzed using one-way ANOVA, followed by Tukey HSD. The statistical analyses were performed using open source programming language R (version 3.6.0). The Mann-Whitney U test was used to compare the performance of old animals exposed to the enriched environment to that of old animals treated with saline and unexposed to the enriched environment.

It was observed that the combination of test compound treatment/administration with the aforementioned enriched environment led to significant increase from baseline levels (i.e. saline controls without enriched environment; FIG. 1B). Overall, these results demonstrate that using the compound of the present invention in combination with a stimulating environment (comparable to a cognitive training) leads to a significant increase of cognitive functions in old animals. It can hence be recognized that the compound of the present invention in combination with a cognitive training can be effectively used to treat, prevent, reduce the symptoms and/or slow down the progression of neurological and/or psychiatric conditions associated with a decline and/or impairment of cognitive functions.

7.3 Example 3: Effects of LSD on Learning Capacity and Memory in Humans

The effects of the test compound (LSD) on cognitive functions in humans—e.g. memory, learning capacity—were investigated by means of a two-dimensional (2D) visuospatial location task in accordance with the experimental design depicted in FIG. 4A. Specifically, the visuospatial location task was carried out as follows:

Thirteen healthy human subjects learned the locations of 15 card pairs taking the test compound (LSD) or placebo in a two-run cross-over open-label design separated by two weeks. Seven subjects received 50 µg of test compound (orally) in the first run and placebo in the second run of the test. Six subjects received placebo in the first run and 50 µg of test compound (orally) in the second run of the test, except for one subject who received 67.5 µg of test compound in the second run.

One hour before receiving either the test compound or placebo, card pairs depicting animals and everyday objects and were presented to the subjects on a table in a 5×6 matrix for learning (learning task; FIG. 4A). During this task, the locations of all 15 card pairs were presented twice. For each card pair, the first card was presented for approximately 1 second, then both cards for about 3 seconds, followed by a 5 to 10-second inter-trial break.

During the subsequent immediate recall task, the first card of each pair was presented and the subjects were asked to turn the correct card in its second location of the matrix. Then the correct location of both cards was shown again for about 2 seconds, irrespective of whether or not the subject was able to locate the correct card. The immediate recall procedure was repeated until the subjects reached a criterion of 60% correct responses, i.e. 60% correct location of the second card of each pair in the matrix.

For the two experimental runs, two parallel versions (versions A and B, respectively) of the task (matrix), each showing different pictures (card pairs) at different locations, were used. Seven subjects were presented version A when administered the test compound and version B when administered the placebo. The other six subjects were presented version A when administered the placebo and version B when administered the test compound. About 24 hours after the learning session, final recall of the memory task was evaluated in a single recall run (recall task). The first card of each pair was presented and the subjects were asked to indicate the location of the second card in the matrix. During the recall task, the first cards were presented to the subjects in a different order from that used during the learning task. The percentage of correctly recalled card locations at final recall relative to the number of correct card locations during the last immediate recall run at learning was determined as the memory performance. The Mann-Whitney's test was used to compare the groups.

The results are shown in FIG. 4B. The performance of the subjects in the 2D visuospatial location task significantly increased when administered with a single dose of the test compound as compared with the placebo. Accordingly, the results indicate that the compound of the present invention increases cognition in humans and can be used to treat, prevent, reduce the symptoms and/or slow down the progression of neurological and/or psychiatric conditions associated with a decline/impairment of cognitive functions.

7.4 Example 4: Dose-Dependent Effects of LSD on Mood and Cognitive Functions in Humans The effects of small doses of the test compound (LSD) administered once on subjective and cognitive functions in human subjects are investigated as follows:

Study design: The study uses a randomized, placebo-controlled, cross-over design. 24 healthy subjects are administered placebo and 3 different doses of LSD (5, 10, and 20 µg) in a randomized, balanced cross-over design. The effects on subjective and cognitive functions are repeatedly measured throughout the study day.

Participants (subjects) visit the laboratory 5 times during 5 weeks. Before the first study day, the subjects come to the laboratory for a "screening visit", which includes a full medical screening by a licensed physician (medical history review, laboratory screening, electrocardiogram recording etc.). The subsequent "study visits" consist in taking the compound (5 µg, 10 µg, or 20 µg of LSD, or placebo), taking blood samples, completing computer tasks, and filling out questionnaires.

Study Population: 24 Healthy Volunteers Aged 18 to 40

The subjective effects of the compound of the present invention are assessed by relying for instance on a 5 Dimensions of Altered States of Consciousness (5D-ASC) (Liechti et al. *Psychopharmacology* 2017, 23, 1499-1510; Studerus et al. *PLoS One* 2010, 5(8), e12412), a Profile of Mood States (POMS) (McNair et al. *POMS Manual for the Profile of Mood States*, Educational and Industrial Testing Service) and/or Visual Analog Scales (VAS) (Morean et al. *Psychopharmacology*, 2013, 227(1), 177-192).

The effects of the compound of the present invention on cognitive functions are assessed by relying, for instance, on a Digit Symbol Substitution Test (DSST), an Instrumental Learning Task (ILT), a Psychomotor Vigilance Task (PVT), a Multifaceted Empathy Test (MET) and/or an Alternate Use Test (AUT). Furthermore, changes in the subject's response to pain during the study are measured by e.g. a Cold Pressor Task (CPT).

Schedule of experimental session: Table 1 provides the schedule of events for each test session (study day).

TABLE 1

| | Schedule of events for each session | | | | | | | | | | |
|---|---|---|---|---|---|---|---|---|---|---|---|
| Time | 09:00 | 09:00 | 09:30 | 10:00 | 10:30 | 11:00 | 11:30 | 12:00 | 13:00 | 14:00 | 16:00 |
| Relative Time (h) | −1 | 0 | 0.5 | 1 | 1.5 | 2 | 2.5 | 3 | 4 | 5 | 6 |
| Substance administration | | | | | | | | | | | |
| LSD/Placebo | | X | | | | | | | | | |
| Psychometrics | | | | | | | | | | | |
| VAS | −1 | 0 | 1 | 2 | 3 | 4 | 5 | 6 | 7 | 8 | 9 |
| POMS, CADSS | 0 | | | 1 | | 2 | | 3 | | 4 | |
| 5D-ASC, EDI | | | | | | | | | | | 1 |

TABLE 1-continued

Schedule of events for each session

| Time | 09:00 | 09:00 | 09:30 | 10:00 | 10:30 | 11:00 | 11:30 | 12:00 | 13:00 | 14:00 | 16:00 |
|---|---|---|---|---|---|---|---|---|---|---|---|
| Blood samples | | | | | | | | | | | |
| Substance concentration | | 0 | 1 | 2 | 3 | 4 | | 5 | 6 | | 7 |
| BDNF | | 0 | | | | 1 | | | 2 | | 3 |
| Autonomic measures | | | | | | | | | | | |
| BP, HR | −1 | 0 | 1 | 2 | 3 | 4 | 5 | 6 | 7 | 8 | 9 |
| Computer tests | | | | | | | | | | | |
| MET, AUT | | | | | | | | 1 | | | |
| DSST, ILT, PVT | | | | | | 1 | | 2 | | | |
| Other assessments | | | | | | | | | | | |
| CPT | | | | | | 1 | | | | | 2 |

Visual analog scales (VAS), profile of mood states (POMS), Clinical administered dissociative states scale (CADSS), altered states of consciousness (5D-ASC), Ego dissolution inventory (EDI), Blood pressure (BP), Heart Rate (HR), Multifaceted Empathy Test (MET), Alternate Use Test (AUT), Digit Symbol Substitution Test (DSST), Instrumental Learning Task (ILT), Psychomotor vigilance task (PVT). Cold pressure task (CPT).

Each of the 4 test sessions lasts for 7 h (Table 1). Subjects are requested to have a light breakfast at home (no caffeine) and to arrive at the laboratory at 9 AM. Pregnancy, drug, and alcohol screens are first performed, using a urine pregnancy and drug test, and breathalyzer. In case of a positive screen for pregnancy or drugs such as cannabis, cocaine, alcohol, opiates, benzodiazepines, amphetamines, psychedelic or dissociative substances etc., subjects are sent home to return at a later time. In case tests are negative, an indwelling intravenous catheter is inserted into a subcutaneous vein of the forearm and baseline measures are obtained.

LSD (5 μg, 10 μg, or 20 μg) or placebo is administered at 10 AM. Outcome measures (see below) are repeatedly assessed during the study session. Subjects are under continuous medical supervision until 6 h after administration and if necessary, are additionally supervised until any alterations of consciousness have completely subsided (<10% of maximum effects on the visual analog scale). There is a washout phase of at least 5 days between each test session (study day).

The study hypothesis is that higher doses of test compound (LSD) are associated with increasingly greater and potentially also qualitatively different subjective effects compared to placebo. It is also hypothesized that doses of greater than 10 μg test compound increase subjective/cognitive functions as compared to placebo. It is hence expected that the compound of the present invention can be effectively used to treat, prevent, reduce the symptoms and/or slow down the progression of neurological and/or psychiatric conditions associated with a decline of cognition.

7.5 Example 5: Effects of Prolonged LSD Administration on Mood and Cognitive Functions in Humans The effects of small doses of the test compound (LSD) administered repeatedly over a period of four weeks (2×12.5 μg/week) on mood, brain activity, learning, neuroplasticity and/or cognitive functions in human subjects are investigated by using electroencephalography (EEG), cognitive tasks, and subjective measures as follows:

Summary of Study Design

This study has a double-blind placebo-controlled between-subjects design with a population of up to 50 healthy subjects (25 vs. 25). Participation includes a "screening visit", eight "study visits" (i.e. study days onto which the test compound/placebo is administered) as well as a "follow-up visit", summing up to ten visits in total. Subjects are randomly assigned to either the placebo or test (LSD) group, each will follow a dosing scheme in which they are administered either placebo or 12.5 μg test compound twice a week over four consecutive weeks.

Cognition and emotional processing are evaluated before, during the study day, and four weeks after administration. EEG is recorded on the screening visit (baseline), on the eight study days, and on the follow-up visit, including resting-state EEG as well as recordings during cognitive tasks. Sensory plasticity is evaluated by EEG on the screening visit, after the second study visit, and on the follow-up visit. Furthermore, safety data (e.g. vital signs, blood tests, blood pressure etc.) are collected throughout the study to evaluate the safety of repeated administrations.

Study Timeline

An overview of the study timeline is depicted in FIG. 5. There must be a minimum of 24 hours between the screening visit and the first study day, to allow for key tests to be performed (e.g. routine blood analyses). Subjects are administered with the test compound/placebo on either Mondays and Thursdays or Tuesdays and Fridays (i.e. there are always two to three resting days between two study days).

Study Days

Two subjects are tested on one study day. The first two subjects are requested to have a light breakfast (no caffeine intake in the 24 hours before coming to the laboratory) and to arrive to the laboratory at 9 AM, and the other two at 10 AM. Pregnancy, drug, and alcohol screens are first performed, using a urine pregnancy and drug test, and breathalyzer. In case of a positive screen for pregnancy or drugs such as cannabis, cocaine, alcohol, opiates, benzodiazepines, amphetamines, psychedelic or dissociative substances etc., subjects are sent home to return at a later time. Food intake is monitored on study days. Besides, healthy snacks and drinks are provided (e.g. fresh squeezed orange juice and other fresh fruits, glucose-containing food like yoghurt and honey etc. so as to maintain normal blood glucose level).

One hour after arriving, the subjects are administered the test compound or placebo (depending on which treatment group they have been assigned). During their stay, the subjects are asked to wait in the patient lounge with clear instructions, e.g. not to converse with other participants, staff etc. "Free-time" is allocated in the afternoon for subjects to engage in activities: the subjects are asked to bring headphones and their favorite music, their own work, something that is of particular interest to them, or computer games. Furthermore, the subjects are provided with material to engage in creative activities, e.g. material to draw and/or paint, musical instruments etc. The type of activities the subjects decide to engage in is recorded and compared across groups. Subjective reports on how the subjects rate the "quality" and/or "productivity" of their allocated freetime are additionally collected.

Measures

Neural electrical activity is recorded using EEG when the subjects are at rest, and also when conducting certain tasks. Key outcomes are changes in oscillatory power and signal complexity between baseline and administration, and between the screening and follow-up visits. The difference in brain activity between the test compound and placebo during cognitive tasks and emotional processing, as well as changes in sensory plasticity induced during a mismatch negativity task and a visual long term potentiation (LTP) task, are investigated. Electrocardiogram (ECG) is recorded during each EEG measurement in order to eliminate artifact from EEG signal.

The subjects are evaluated by means of well-established cognitive tasks and/or "real-life" activities. For instance, the subjects are evaluated in respect of their sensory plasticity (Visual LTP, Roving Mismatch Negativity (MMN)), attention (SART or Oddball), learning and memory (Mallas Memory Task (long term), Paired associate learning task, Go Game), problem solving (Matrix Reasoning), emotional processing (Multifaceted Empathy Test, Physiological and subjective response to multi-modal emotional stimuli, Cold pressor task) and/or cognitive flexibility/creativity/exploratory behavior (IDED (cognitive flexibility), Alternate Use Task, Picture concept, VR environment exploring (e.g. explore/exploit paradigm)).

Blood samples for laboratory safety are collected on the screening visit (2×5 ml). Further blood samples are collected at regular times after administration on study days 1 and 8, to determine test compound plasma concentration. Blood samples for plasma concentration are centrifuged and plasma is frozen at −20° C. until further analysis for pharmacokinetic assessments. Whole blood samples are taken to measure brain-derived neurotrophic factor (BDNF) (4×5 ml, EDTA blood per study day). BDNF will be measured 4 times per day on dosing day 1, 4 and 8. [possible inclusion of cortisol and TNF-alpha level analysis]. Blood pressure and heart rate are monitored on each study day, at baseline as well as 2 h and 5 h after administration.

Primary Outcomes

It is expected that subjects administered with the test compound (LSD group) show changes (increase) in cognitive functions and/or mood after four weeks as compared to subjects administered with placebo.

Secondary Outcomes

Furthermore, it is expected that subjects administered with the test compound (LSD group) show one or more of the following:

1. Difference in resting-state brain activity between test compound vs. placebo as measured with EEG. It is expected that the LSD group shows a decrease in alpha power during rest compared to the placebo group;
2. Changes in subjective measures after four weeks compared to baseline for test compound vs. placebo. It is expected that the LSD group shows an increase in the mean well-being scores between follow-up and baseline compared to the placebo group;
3. Differences in LTP-like enhancement of the visually evoked potential between test compound vs. placebo, as measured with EEG. It is expected that LTP is enhanced after LSD administration compared to placebo;
4. Performance on cognitive tasks during test compound vs. placebo. It is expected that performance on the cognitive tasks is enhanced under LSD compared to placebo;
5. Difference in brain activity between test compound vs. placebo measured with EEG during cognitive tasks;
6. Subjective effects during test compound vs. placebo. The LSD group expectedly shows elevated levels in positive mood and vitality;
7. Incremental improvements in a learning task for test compound vs. placebo. It is expected that the ability to learn is enhanced in the LSD group compared to placebo, as reflected by larger improvements in task performance (i.e. reduced number of moves and time to solve problems) between baseline and follow-up for the LSD group compared to placebo.

7.6 Example 6: Effects of Prolonged LSD Administration on Mood and Cognitive Functions in Elderly Humans with or without MCI Symptoms Herein the effects of the test compound (LSD) on cognitive functions in healthy aging and mild cognitive impairment (MCI) in elderly humans (i.e. 60 years old or more) are investigated.

80 subjects aged over 60 are recruited: 40 subjects with a diagnosis of MCI (as described by O'Caoimh et al. in *Journal of Alzheimer's Disease* 2016, 51, 619-629) and 40 aged-matched healthy subjects. The groups are split in two, and allocated to an active study (test compound) group or a placebo. The study group is administered up to 15 μg of test compound twice a week over 4 weeks. During the 4-week administration, the subjects are asked to perform once every 1 to 3 days or on a daily basis spatial orientation tasks and/or inductive reasoning tasks as described above.

The subjects are then evaluated with respect to one or more of the following aspects: brain plasticity (e.g. TMS/EEG), blood markers of plasticity, hormonal changes (e.g. cortisol), learning and memory, vitality, mobility, motivation, apathy etc.

7.7 Example 7: Effects of LSD Administration on BDNF Blood Serum Levels in Healthy Volunteers The present double-blind placebo-controlled, within-subjects study aimed to investigate whether low doses (0, 5, 10, and 20 mcg) of LSD affect brain-derived neurotrophic factor (BDNF) blood levels in healthy volunteers. Blood samples were collected every two hours over a six-hour period, and BDNF levels were determined afterwards in blood serum.

BDNF is a protein found in the brain and the periphery. BDNF acts on certain neurons of the central nervous system and the peripheral nervous system, helping to support survival of existing neurons, and encouraging growth and differentiation of new neurons and synapses. In the brain, it is active in the hippocampus, cortex, and basal forebrain-areas vital to learning, memory, and higher thinking. BDNF is also expressed in the retina, kidneys, prostate, motor neurons and skeletal muscle and it is also found in saliva. Although the vast majority of neurons in the mammalian brain are formed prenatally, parts of the adult or elderly brain retain the ability to grow new neurons from neural stem cells in a process known as neurogenesis. Neurotrophins such as BDNF help stimulating and controlling neurogenesis. Furthermore, BDNF enhances synaptogenesis.

Procedure

Twenty-four recreational psychedelic users were included in this study. Prior to inclusion, participants underwent medical screening including standard blood chemistry, hematology and urinalysis. Inclusion criteria were written informed consent; age 18-40 years; previous experience with a psychedelic drug, but not within the past three months; proficient knowledge of the English language; good physical health; free from psychotropic medication; BMI between 18-28 kg/m². Exclusion criteria were history of drug abuse or addiction as assessed using the DSM-IV criteria; history of psychiatric and neurological disorders; previous experience with serious side effects to psychedelic drugs (anxiety or panic attacks); cardiovascular abnormalities; hypertension; psychotic disorder in first-degree relatives; tobacco smoking (>20 cigarettes/day; excessive alcohol (>20 alcoholic consumptions/week); pregnancy or lactation.

LSD doses used were 5, 10, and 20 mcg LSD base. LSD doses were dissolved in ethanol (96% Vol) resulting in a 1 mL volume and the placebo solution consisted of 1 mL of ethanol only. Test days were scheduled with a minimum of five days in between doses. A test day started at 9:00 AM with a screen for the presence of drugs of abuse in urine (THC/opiates/cocaine/amphetamines/methamphetamines), and alcohol in breath. Women were submitted to a urine pregnancy test. When tests were negative, a venous catheter was placed to draw blood and LSD or placebo was administered orally at 10:00 AM. The study was conducted according to the code of ethics on human experimentation established by the declaration of Helsinki (1964) and the World Medical Association (2013).

BDNF Determination

Blood samples were taken at −0.5 h, +2 h, +4 h and +6 h relative to drug administration; samples were centrifuged, and serum was transferred into a clean tube and frozen subsequently at −20° C. until analysis. BDNF determination was assessed using an ELISA kit (Biosensis Mature BDNF Rapid ELISA kit: human, mouse, rat; Thebarton, Australia) as described by Akinomoto et al. in *Behavioural Brain Research* 2019, 359, 342-352.

Statistical Analysis

Difficulties with the peripheral venous catheter during blood sample collection resulted in missing data. Therefore, only complete within-subjects (WS) cases entered analyses, using the statistical program SPSS (version 25.0). Non-parametric bootstrapped paired-samples t-tests with trapezoidal calculated AUC's as dependent variable were used for 5 mcg (N=10), 10 mcg (N=9), and 20 mcg (N=8), and corresponding placebo. Furthermore, LSD-placebo contrasts were examined using BDNF serum levels at 0 h, +2 h, +4 h and +6 h after dose administration using non-parametric bootstrapped paired samples t-tests. Lastly, to examine time effects per dose, non-parametric bootstrapped repeated measures ANOVA (0 h, +2 h, +4 h, and +6 h) was used, with subsequent non-parametric bootstrapped paired samples t-tests.

RESULTS & DISCUSSION

BDNF AUC levels were significantly increased following all LSD doses (5 mcg: Z=−2.29, p=0.02; 10 mcg: Z=−2.67, p<0.01; 20 mcg: Z=−2.52, p<0.01) compared to placebo (FIG. 6A). More specifically, non-parametric t-tests revealed higher BDNF levels at +4 h after 5 and 10 mcg LSD administration (Z=−2.80, p<0.01; Z=−1.95, p=0.05), and at +6 h after 5 mcg and 20 mcg LSD administration at (Z=−2.29, p<0.01; Z=−2.52, p=0.01) compared to placebo (FIG. 6B-D). BDNF levels following placebo were stable throughout the test day. Peak BDNF levels were observed at four hours after administration of 5 mcg LSD (8.95 ng/mL), and at six hours after administration of 10 mcg (8.28 ng/mL) and 20 mcg LSD (11 49 ng/mL).

This study provides evidence that low doses of LSD increase BDNF serum levels in subjects up to 6 hours after administration, indicating a potential for cognitive enhancement, in particular if combined with a cognitive training. The study provides evidence of neuroplasticity in humans after low doses of an ergoline derivative (LSD). It is believed that taking advantage of the substance-induced neuroplasticity by providing a cognitive training leads to sustained cognitive enhancement, thereby enabling the treatment of neurological and/or psychiatric disorders, such as MCI and Alzheimer's disease.

The invention claimed is:

1. A method of treating, preventing, reducing the symptoms of, or slowing the progression of a neurological and/or psychiatric disorder in a subject, comprising:
   a. administering to the subject a therapeutically effective amount of a lysergamide, or a pharmaceutically acceptable salt thereof; and
   b. providing the subject with a cognitive training.

2. The method of claim 1, wherein the lysergamide is administered in an amount of
   a. 30 to 100 µg per day, or
   b. 40 to 75 µg per day.

3. The method of claim 1, wherein the cognitive training comprises one or more of a criterion task, near-transfer task, far transfer task, updating task, span task, knowledge task, spatial orientation task, inductive reasoning task, and spatial memory task.

4. The method of claim 1, wherein the cognitive training is provided 1 to 10 times per day.

5. The method of claim 1, wherein the lysergamide is administered in an amount of 50 µg per day, and wherein the administering occurs every 1 to 6 days over a period of up to 30 days, up to 60 days, up to 180 days, or up to 600 days.

6. The method of claim 1, wherein the cognitive training is provided at one or more points relative to the administering step, and wherein the providing occurs at one or more of: concurrently with, before, and after administering the lysergamide.

7. The method of claim 1, wherein the neurological disorder is selected from dementia, mild cognitive impairment (MCI), Alzheimer's disease, frontotemporal degeneration, Lewy body disease, Parkinson's disease, vascular dementia, prion disease, Huntington's disease, dementia/neurocognitive issues due to an HIV infection, post-operative cognitive decline, post-operative dementia, multiple sclerosis, amyotrophic lateral sclerosis (ALS), spinocerebellar ataxia (SCA), neuronal ceroid lipofuscinosis (NCL), chronic fatigue syndrome, brain injury, central and/or peripheral neuropathy, and stroke; and the psychiatric disorder is selected from anxiety, a disorder of the obsessive compulsive spectrum, mania, body dysmorphic disorder, phobias, substance addiction, alcohol addiction, opioid addiction, benzodiazepine addiction, a behavioral addiction, gambling addiction, binge eating disorder, premenstrual dysphoric disorder, seasonal affective disorder, an adjustment disorder, bipolar disorder, and borderline personality disorder.

8. The method of claim 7, wherein the neurological disorder is selected from MCI and Alzheimer's disease.

9. The method of claim 1, wherein the subject is a human subject.

10. The method of claim 9, wherein the subject has a score of from 10 to 26 points, from 12 to 24 points, from 18 to 23 points, or 22 points in a Montreal Cognitive Assessment (MoCA).

11. The method of claim 1, further comprising administering an additional therapeutic agent, an additional therapy, or a combination thereof, wherein the additional therapeutic agent is selected from an acetylcholinesterase inhibitor, an NMDA receptor inhibitor, an antidepressant, an anxiolytic, and a cannabinoid; and the additional therapy is selected from transcranial magnetic stimulation (TMS), electroconvulsive therapy, deep brain stimulation, behavioral therapies, mindfulness, acceptance and commitment therapy (ACT), cognitive behavioral therapy (CBT), biofeedback, and hypnosis.

12. The method of claim 1, wherein the lysergamide is lysergic acid 2-butyl amide, lysergic acid 2-pentyl amide, lysergic acid 3-pentyl amide, lysergic acid 2-hexyl amide, N,N-diallyl lysergamide, lysergic acid methylisopropyl amide, lysergic acid diethylamide (LSD), 6-ethyl-6-nor-lysergic acid diethylamide, 6-propynyl-6-nor-lysergic acid diethylamide, 6-allyl-6-nor-lysergic acid diethylamide, 6-propyl-6-nor-lysergic acid diethylamide, 6-cyclopropyl-6-nor-lysergic acid diethylamide, 6-butyl-6-nor-lysergic acid diethylamide, 1-acetyl lysergic acid diethylamide, 1-propionyl lysergic acid diethylamide, 1-propionyl-6-ethyl-6-nor-lysergic acid diethylamide, N-morpholinyl lysergamide, N-pyrrolidyl lysergamide, N-piperidyl lysergamide, or lysergic acid 2,4-dimethylazetidine.

13. The method of claim 12, wherein the lysergamide is LSD.

14. The method of claim 9, wherein the subject is a young adult, a middle-aged adult, or an older adult.

15. The method of claim 1, wherein the subject has a genetic predisposition and/or a family history of a neurological and/or psychiatric disorder.

16. The method of claim 1, wherein the lysergamide is administered to the subject orally, sublingually, parenterally, mucosally, nasally, topically, or by inhalation.

17. The method of claim 4, wherein the cognitive training is provided 1 to 3 times per day.

18. The method of claim 1, wherein the cognitive training is provided every 1 to 7 days.

19. The method of claim 18, wherein the cognitive training is provided every 1 to 3 days.

20. The method of claim 19, wherein the cognitive training is provided every day.

* * * * *